(12) United States Patent
Odland et al.

(10) Patent No.: US 7,935,092 B1
(45) Date of Patent: May 3, 2011

(54) SELF-INTRODUCING INJECTION AND ASPIRATION DEVICE

(75) Inventors: Rick Mathew Odland, Roseville, MN (US); Scott R. Wilson, Maple Grove, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 366 days.

(21) Appl. No.: 11/492,386

(22) Filed: Jul. 25, 2006

(51) Int. Cl.
*A61M 5/32* (2006.01)
*A61N 1/30* (2006.01)
*A61M 3/00* (2006.01)
*A61M 29/00* (2006.01)

(52) U.S. Cl. .......... 604/272; 604/20; 604/43; 604/96.01

(58) Field of Classification Search .............. 604/9, 272, 604/264
See application file for complete search history.

(56) References Cited

U.S. PATENT DOCUMENTS

| | | | |
|---|---|---|---|
| 4,411,657 A | 10/1983 | Galindo | 604/274 |
| 5,049,132 A * | 9/1991 | Shaffer et al. | 604/101.02 |
| 5,370,610 A * | 12/1994 | Reynolds | 604/43 |
| 5,425,723 A | 6/1995 | Wang | 604/280 |
| 5,709,653 A * | 1/1998 | Leone | 604/20 |
| 5,800,407 A | 9/1998 | Eldor | 604/264 |
| 6,030,358 A | 2/2000 | Odland | 604/27 |
| 6,241,710 B1 | 6/2001 | VanTassel et al. | 604/272 |
| 6,350,253 B1 | 2/2002 | Deniega et al. | 604/164.02 |
| 6,537,194 B1 * | 3/2003 | Winkler | 600/3 |
| 6,537,241 B1 | 3/2003 | Odland | 604/9 |
| 6,547,769 B2 | 4/2003 | VanTassel et al. | 604/272 |
| 6,758,828 B2 * | 7/2004 | Hammer et al. | 604/43 |
| 6,855,132 B2 | 2/2005 | VanTassel et al. | 604/272 |
| 6,949,087 B2 | 9/2005 | VanTassel et al. | 604/272 |
| 6,960,648 B2 | 11/2005 | Bonny | 530/330 |
| 6,969,373 B2 | 11/2005 | Schwartz et al. | 604/170.03 |
| 7,241,286 B2 * | 7/2007 | Atlas | 604/537 |
| 2001/0023349 A1 * | 9/2001 | VanTassel et al. | 606/53 |
| 2003/0036728 A1 * | 2/2003 | Samson et al. | 604/103.01 |
| 2005/0187525 A1 | 8/2005 | Hilgers et al. | 604/264 |

* cited by examiner

*Primary Examiner* — Nicholas D Lucchesi
*Assistant Examiner* — Ian K Holloway
(74) *Attorney, Agent, or Firm* — Fredrikson & Byron, P.A.

(57) ABSTRACT

A self-introducing medical device that can be used for delivering drugs or other therapeutic fluids at a uniform rate over an extended area to an internal anatomical location of a patient's body. The device can also be used for aspirating excess fluid from an internal anatomical location of a patient's body.

18 Claims, 11 Drawing Sheets

SELF-INTRODUCING INJECTION AND ASPIRATION DEVICE

FIELD OF THE INVENTION

The invention generally relates to devices used to inject or aspirate therapeutic and/or biological fluids and more specifically to devices capable of introduction into a patient without the use of additional introducing devices.

BACKGROUND

Indwelling catheters and other devices are commonly implanted into patients for varying lengths of time and used for many medical procedures including therapeutic and diagnostic fluid delivery and aspiration of excess fluid and are well known in the art. The simplest such devices typically allow the exit of fluid through a single opening located at the distal tip of a needle. A needle presents problems wherein relatively high pressure fluid is delivered and has a highly concentrated distribution near the opening and typically does not leach out to more distant locations. An attempt to improve the delivery of fluid includes catheters having a plurality of openings at various axial positions along the distal portion of the catheter. The effectiveness of such devices for some procedures is limited due to uneven weep rates resulting from higher fluid pressure in the area of the proximal holes than at more distal holes. A further disadvantage of such catheter-like devices is that they are inherently relatively soft and therefore require a guidewire, guide catheter, cannula, trocar or other type of introducer to initially position the device prior to treatment. Being forced to use additional introducing devices necessitates longer treatment times, increased expense and a greater probability of infection. In addition, the need for introducing devices increases the size of tissue access opening to the treatment site, thereby increasing the morbidity, invasiveness and pain associated with the procedure. Other catheters provide for a more uniform weep rate by having an infusion catheter with an outer tube and a concentrically enclosed inner tube, and a central lumen in the inner tube. Both the outer and inner tubes are provided with a plurality of openings along a distally located infusion section which even the longitudinal distance the fluid must flow before being infused into a patient. As discussed above, this and similar catheters are inherently relatively soft and therefore require a guidewire, guide catheter, cannula, trocar or other type of introducer to initially position the device prior to treatment.

The recent advent of Botox® treatment for the elimination of wrinkles in ageing skin is ordinarily performed by a physician injecting the treatment area with diluted amounts of the toxin produced by the bacterium *Clostridium botulinum*. The toxin is typically injected beneath the skin into specific muscles using a conventional needle attached to a syringe, which results in a relatively concentrated amount of toxin in a small area, with reduced amounts leaching to more distant locations. The affected muscles are weakened in a controlled manner thereby temporarily being unable to contract, giving the appearance of a skin wrinkle disappearing. For purposes of Botox® treatment as well as many other medical procedures, it would be extremely desirable to have a temporarily implantable device that is inherently rigid so as to be self-introducing, which allows the uniform distribution of therapeutic fluids over a relatively large surface area. Also desirable would be a self-introducing device that could be used under negative pressure to aspirate or remove excess body fluid from a region of a patient's body. A single device that could evenly distribute effective concentrations of a therapeutic fluid over an extended area and also used to aspirate excess fluid amounts would be even more desirable.

Hollow fibers are made from porous polymers that were developed to improve the distribution of drugs administered directly into the central nervous system. It has been found that using a porous polymer hollow fiber significantly increases the surface area of brain tissue that the drug or therapeutic fluid is infused into. Dye was infused into a mouse brain by convection-enhanced delivery using a 28 gauge needle compared to a hollow fiber having a 3 mm length. Hollow fiber mediated infusion increased the volume of brain tissue labeled with dye by a factor of 2.7 times compared to using a needle. In order to determine if hollow fiber use could increase the distribution of gene therapy vectors, a recombinant adenovirus expressing the firefly luciferase reporter was injected into the mouse striatum. Gene expression was monitored using in vivo luminescent imaging. In vivo imaging revealed that hollow fiber mediated infusion of adenovirus resulting in gene expression that was an order of magnitude greater than when a conventional needle was used for delivery. To assess distribution of gene transfer, an adenovirus expression green fluorescent protein was injected into the striatum using a hollow fiber and a conventional needle. The hollow fiber greatly increased the area of brain transduced with adenovirus relative to a needle, transducing a significant portion of the injected hemisphere.

SUMMARY

In one embodiment, the injection/aspiration device comprises a catheter having a hollow member defining a lumen and a distal end. At least one opening extends through the hollow member allowing fluid communication between the lumen and an outer surface of the hollow member. The hollow member is sufficiently rigid to allow the catheter to be introduced into a patient without the use of another device. A semi-permeable membrane is attached to the outer surface of the hollow member and covers the at least one opening, and defines a pore structure allowing fluid communication between the lumen and an area outside the semi-permeable membrane.

In another embodiment, the injection/aspiration device comprises a catheter having a first substantially rigid hollow member which defines an outer dimension, a lumen and a distal end. At least one opening extends through the first hollow member allowing fluid communication between the lumen and an outer surface of the hollow member. A second substantially rigid hollow member defines an inner dimension sufficiently large to surround the outer dimension of the first hollow member and surrounds the first hollow member. A semi-permeable membrane is attached to the outer surface of the first hollow member and covers the at least one opening extending through the first hollow member, the semi-permeable membrane defining a pore structure allowing fluid communication between the lumen and an area outside the semi-permeable membrane. The first hollow member and second hollow member together are sufficiently rigid to allow the catheter to be introduced into a patient without the use of another device.

DETAILED DESCRIPTION

The particulars shown herein are by way of example and for purposes of illustrative discussion of the invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.

NOMENCLATURE

10 Injection/Aspiration Device
12 Hollow Member
13 Outer Surface of Hollow Member
14 Semi-Permeable membrane
16a Bonding Agent (Proximal Layer)
16b Bonding Agent (Distal Layer)
18 Opening
20 Lumen
22 Distal End
24 Plug
26 Fluid Collection Chamber
28 Arrow Depicting Positive Fluid Pressure in Lumen
29 Arrow Depicting Fluid Passing Through Opening
30 Arrow Depicting Fluid Passing Through Semi-Permeable Membrane to Patient
32 Arrow Depicting Negative Pressure in Lumen
33 Arrow Depicting Fluid Passing Through Opening Into Lumen
34 Arrow Depicting Fluid Passing Through Semi-Permeable Membrane Into Fluid Collection Chamber
36 Connector
40 Syringe
50 Patient
100 Injection/Aspiration Device
102 First Hollow Member
104a Second Hollow Member (Proximal Section)
104b Second Hollow Member (Distal Section)
106 Semi-Permeable membrane
108 Fluid Collection Chamber
110a Bonding Agent (Proximal Layer)
110b Bonding Agent (Distal Layer)
112 Distal End
114 Opening
116 Arrow Depicting Positive Fluid Pressure
118 Arrow Depicting Fluid Passing Through Opening
120 Arrow Depicting Fluid Passing Through Semi-Permeable Membrane to Patient
122 Arrow Depicting Negative Pressure in Lumen
124 Arrow Depicting Fluid Passing Through Opening Into Lumen
126 Arrow Depicting Fluid Passing Through Semi-Permeable Membrane Into Fluid Collection Chamber
128a Outer Surface of Proximal Section of Second Hollow Member
128b Outer Surface of Distal Section of Second Hollow Member
130 Second Lumen
132 First Lumen
134 Plug
200 Injection/Aspiration Device
212 Hollow Member
213 Outer Surface of Hollow Member
214 Semi-Permeable Membrane
216 Bonding Agent
218 Opening
220 Lumen
222 Distal End
224 Plug
226 Fluid Collection Chamber
400 Injection/Aspiration Device
402 First Hollow Member
404a Second Hollow Member (Proximal Section)
404b Second Hollow Member (Distal Section)
406 Semi-Permeable Membrane
408 Fluid Collection Chamber
410a Bonding Agent (Proximal Layer)
410b Bonding Agent (Distal Layer)
412 Distal End
414 Opening

DEFINITIONS

"Catheter" is used in its general sense and refers to a conduit capable of transporting a substance or fluid to a remote location.

"Distal" means further from the point controlled by the operator (e.g., physician or technician) of a device.

"Fluid" means a substance offering no permanent resistance to change of shape, such as a gas or a liquid.

"Proximal" means closer to the point controlled by the operator (e.g., physician or technician) of a device.

"Semi-Permeable Membrane" means a porous or semi-permeable barrier permitting controlled passage of fluid molecules under certain conditions.

Construction

Figure 1:
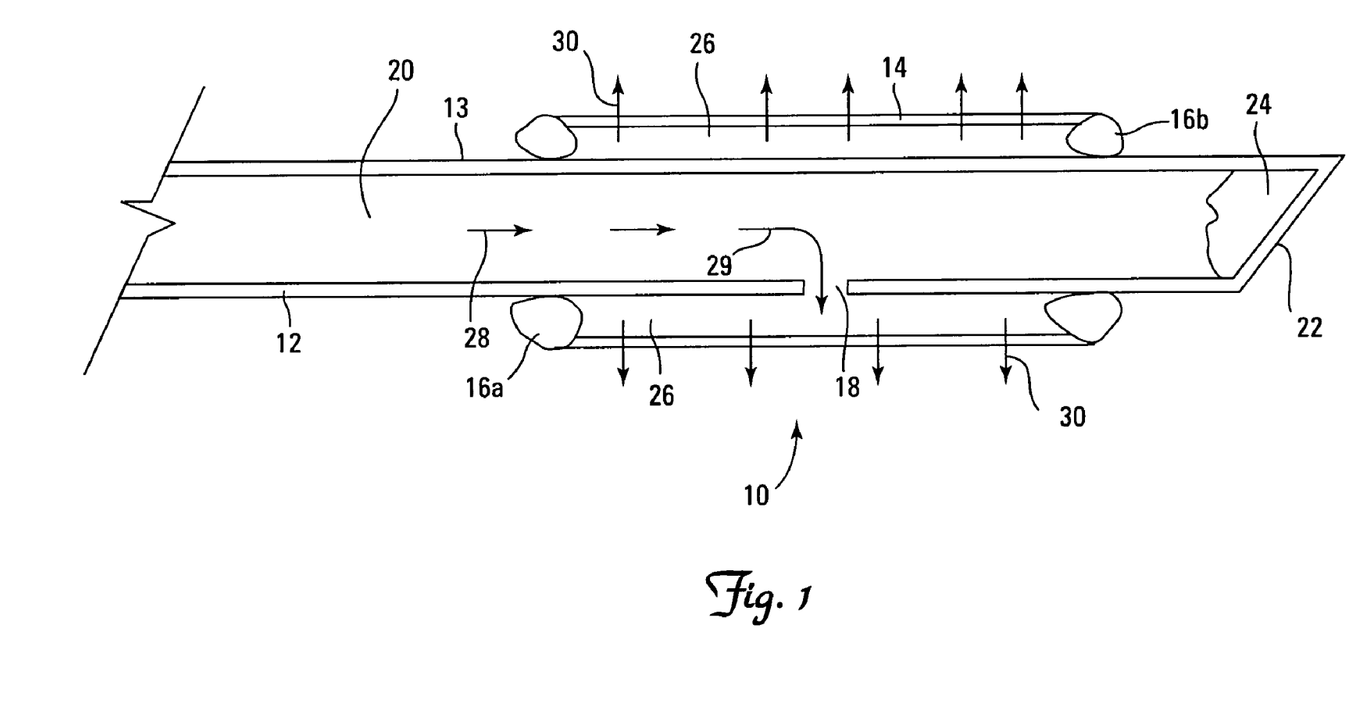
FIG. 1 is a cross sectional centerline view taken along the longitudinal axis of the hollow member of an embodiment of the injection/aspiration device, showing fluid passing through the semi-permeable membrane resulting from positive pressure applied to the lumen.

FIG. 1 is a cross sectional centerline view taken along the longitudinal axis (unnumbered) of the hollow member 12 of an embodiment of the injection/aspiration device 10. The hollow member 12 is formed from a substantially rigid material such as structural materials with a high modulus, including metals, polymers, (with and without fiber reinforcement) and ceramics and defines an outer surface 13 and a lumen 20, with the lumen 20 allowing fluid communication through the hollow member 12. A semi-permeable membrane 14 covers at least a single opening 18 through the hollow member 12 and at least partially covers the hollow member 12 to form a fluid collection chamber 26 between the hollow member 12 and semi-permeable membrane 14 and is attached to the hollow member 12 by a proximal layer 16a and a distal layer 16b of a bonding agent. The bonding agent 16a, 16b includes but is not limited to structural adhesives such as epoxies, urethanes, acrylics, polyimides and polysulfones. The opening 18 is formed through the hollow member 12 allowing fluid communication between the lumen 20 and fluid collection chamber 26 as depicted by arrow 29 (arrow 33 in FIG. 2). While the semi-permeable membrane 14 is shown in this embodiment as being on the exterior surface 13 of the hollow member 12, the invention also contemplates having the semi-permeable membrane 14 placed on an interior surface (not shown), which embodiment is therefore within the scope of the invention. The hollow member 12 defines a distal end 22 which in this embodiment is sealed by plug 24.

The injection/aspiration device 10 shown in FIG. 1 is depicted by arrow 28 as having positive fluid pressure applied to the lumen 20. This results in fluid (not shown) moving distally through the lumen 20 and ultimately through the opening 18 (as depicted by arrow 29), into the fluid collection chamber 26 and finally outward through the porous semi-permeable membrane 14 at a relatively uniform pressure and distribution to the intended treatment site of the patient, as a result of buffering through the fluid collection chamber 26.

Figure 2:
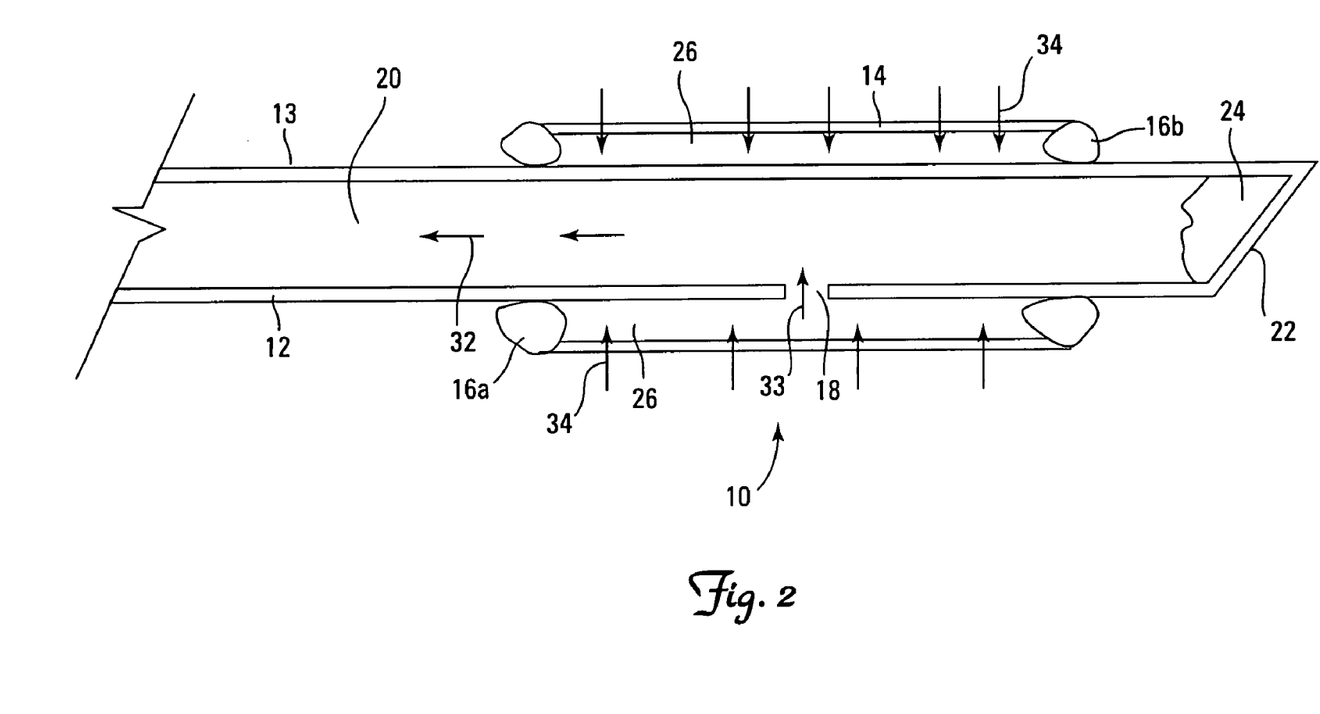
FIG. 2 is a cross sectional centerline view taken along the longitudinal axis of the embodiment of the injection/aspiration device shown in FIG. 1, showing fluid from a patient passing through the semi-permeable membrane into the fluid collection chamber, resulting from negative pressure applied to the lumen.

The injection/aspiration device 10 shown in FIG. 2 is depicted by arrow 32 as having negative pressure applied to the lumen 20. This results in fluid (not shown) moving through the semi-permeable membrane 14 as depicted by arrow 34, into the fluid collection chamber 26, through the opening 18 (as depicted by arrow 33), and finally into the lumen 20 where the fluid (not shown) is withdrawn.

The hollow member 12 is cut to length with the ends machined for final uses that typically include a sharpened needle tip on the distal end 22 for penetrating tissue and a connector 36 at the proximal end (unnumbered) used to connect the device 10 to other devices. The opening 18 is created by conventional machine cutting tools (e.g., drill bits) or other types of hole drilling processes such as laser machining. The semi-permeable membrane 14 is slid over and then bonded 16a, 16b at both ends to the hollow member 12. The distal end 22 is plugged with filling material such as adhesives, solder or brazing alloys.

Figure 3:
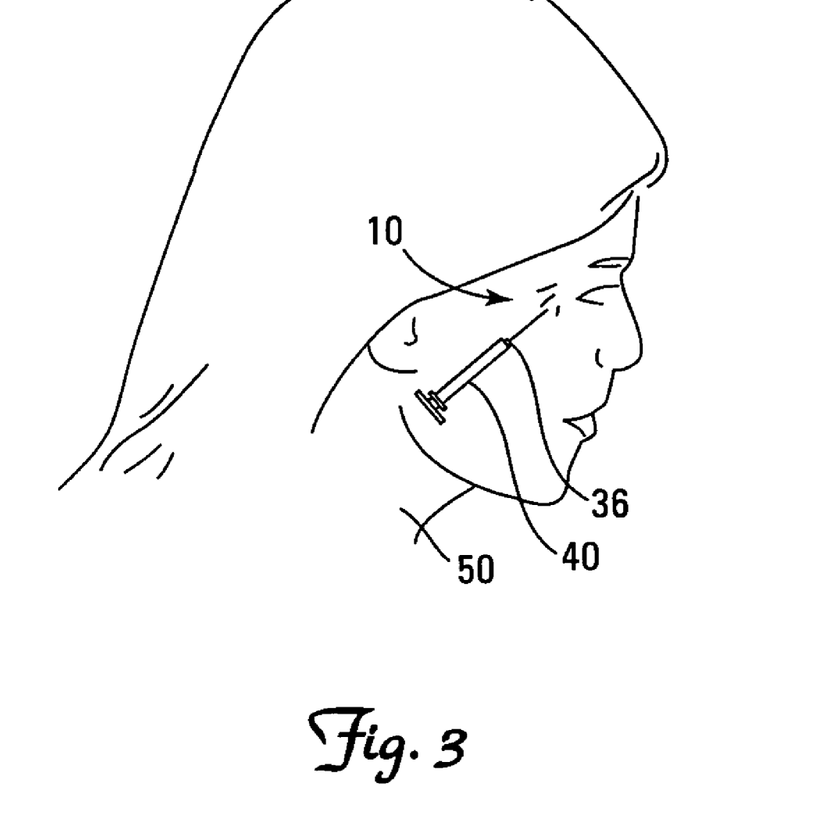
FIG. 3 is a side view of the injection/aspiration device being used in a subcutaneous therapeutic fluid delivery treatment to a patient.

FIG. 3 shows a side view of the injection/aspiration device 10 being used to deliver a Botox® injection to a patient. It is understood that the injection/aspiration device 10 could also be used for many other treatments requiring a uniform, controlled delivery of a therapeutic fluid including a more interior anatomical location, thus the invention is not limited to only Botox® injections. It is further understood that the injection/aspiration device 10 is not limited to injecting therapeutic fluid into a patient but can also be used for aspirating excess fluid.

Figure 4:
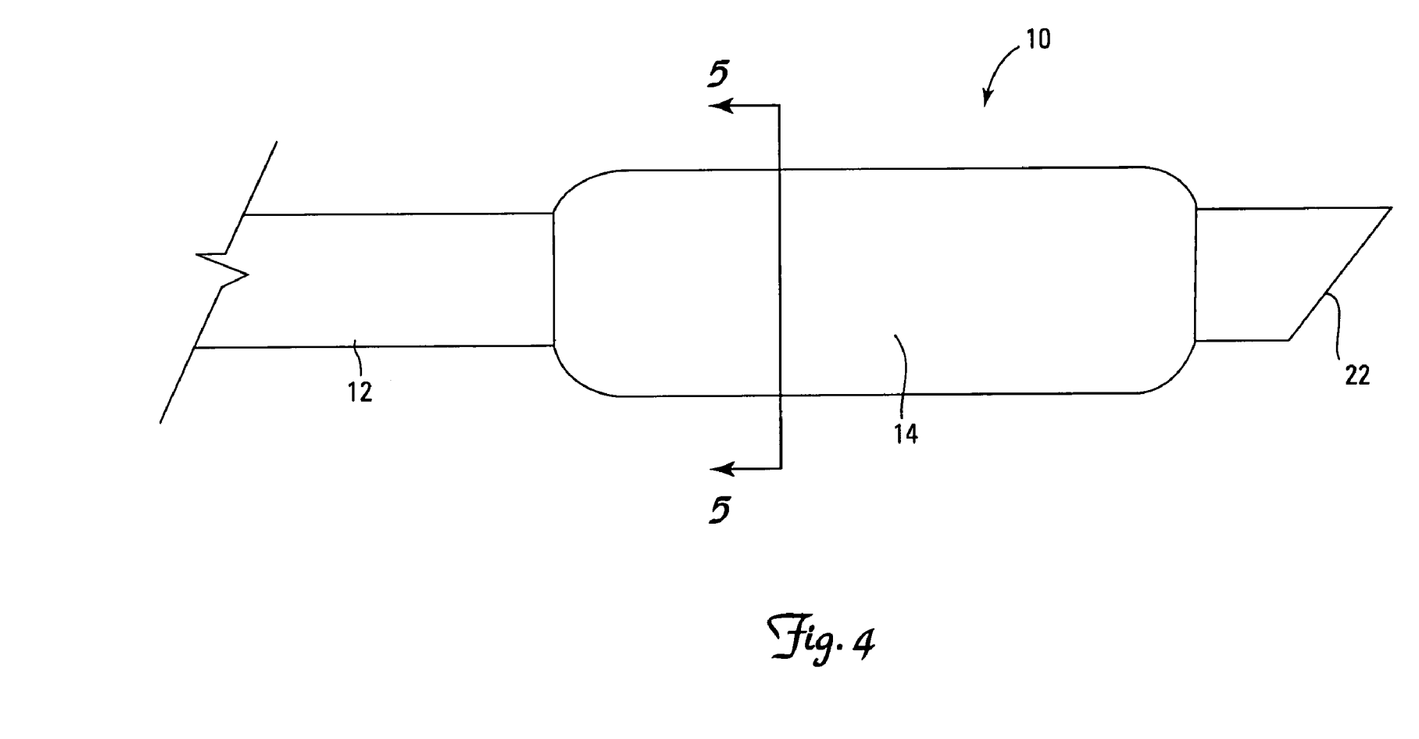
FIG. 4 is an external side view of the injection/aspiration device shown in FIGS. 1-3.

FIG. 4 is an external side view of the injection/aspiration device 10 prior to use. The semi-permeable membrane 14 externally surrounds the hollow member 12 at least at a point covering the opening 18 (opening not shown this drawing). It is understood that the proximal end of the device (not shown) is provided with a connector 36 such as a Luer (not shown), barbed (not shown), or tapered tube (not shown) fitting allowing it to be connected with a fluid supply and pressure generating device such as a syringe 40. It is further understood that the device could also be connected with a vacuum or aspirating device (not shown) such as a mechanical pump (not shown) or hand operated syringe 40 when the device 10 is used for aspirating fluids.

Figure 5:
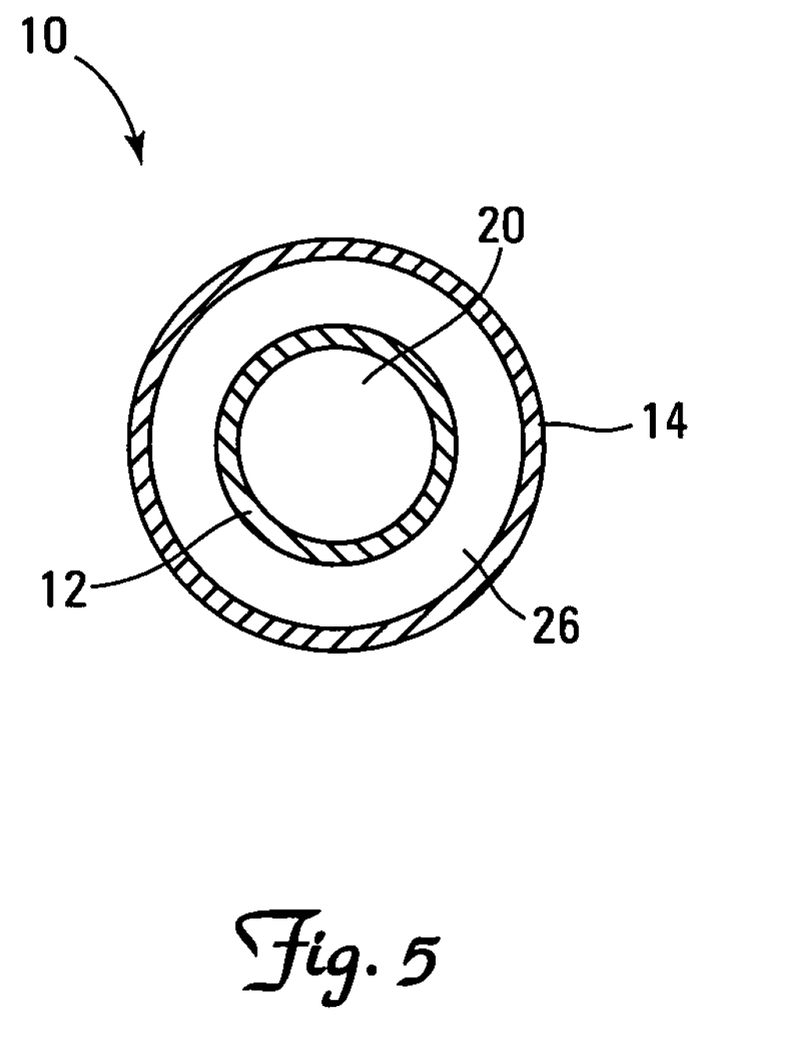
FIG. 5 is a cross sectional view of the injection/aspiration device shown in FIGS. 1-4 taken through line 5-5 of FIG. 4.

FIG. 5 is a cross sectional view of the invention shown in FIGS. 1-4 taken through line 5-5 of FIG. 4. It is seen that the first hollow member 12 is substantially concentrically surrounded by the semi-permeable membrane 14 at the point where the cross section is taken. Fluid (not shown) is pressurized through the lumen 20 until it reaches the sealed distal end 22 and is then forced back and out through the opening 18, into the fluid collection chamber 26 and finally through the pore structure (not shown) of the semi-permeable membrane 14 into the patient for treatment. It is understood that while a concentric, circular configuration is shown in the drawings, this is for purposes of illustration only and many other shapes and/or configurations (not shown) could also be effectively used. Possible configurations include tubes, which are most common but could also include triangular, square, rectangular, other multi-segmented geometrical polygons, or composite profiles combining different segment lengths and/or shapes.

Figure 11:
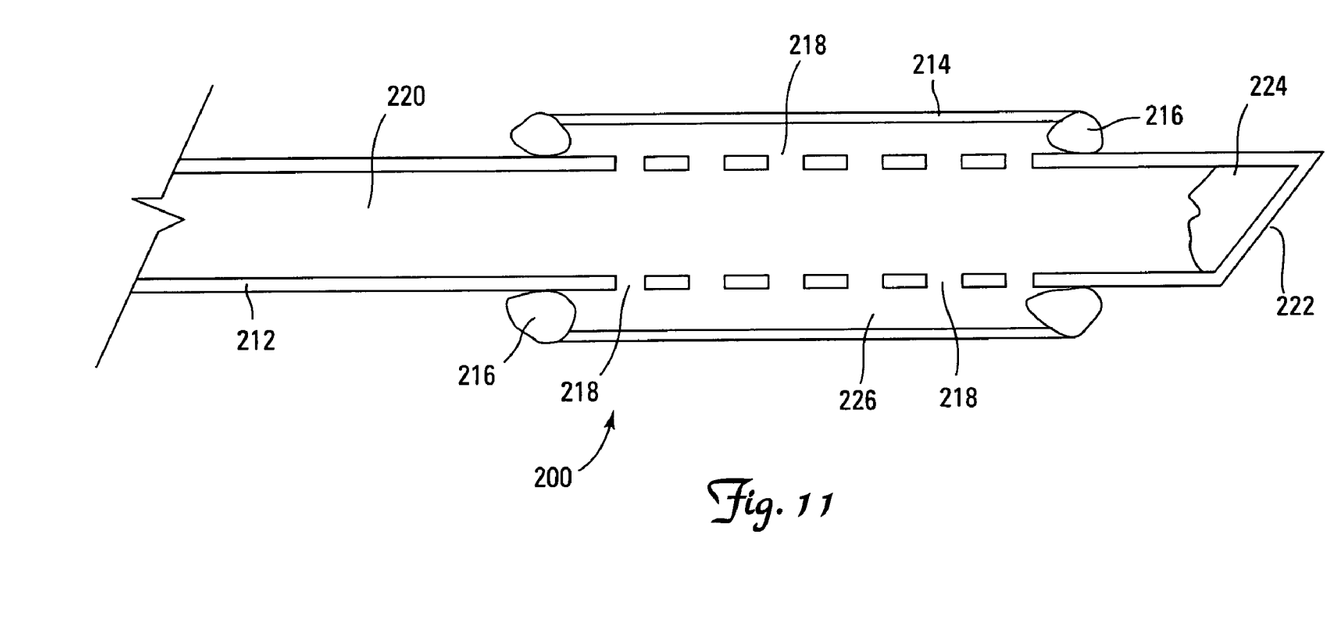
FIG. 11 is a cross sectional centerline view taken along the longitudinal axis of the hollow member of an embodiment of the injection/aspiration device having a plurality of openings in the hollow member that is otherwise similar to the embodiment shown in FIGS. 1-5.

FIG. 11 is a cross sectional centerline view taken along the longitudinal axis of the hollow member 212 of an embodiment of the injection/aspiration device 200 having a plurality of openings 218 in the hollow member 212. Other than having a plurality of openings 218 the injection/aspiration device 200 is similar to the injection/aspiration device 10 shown in FIGS. 1-5.

Figure 6:
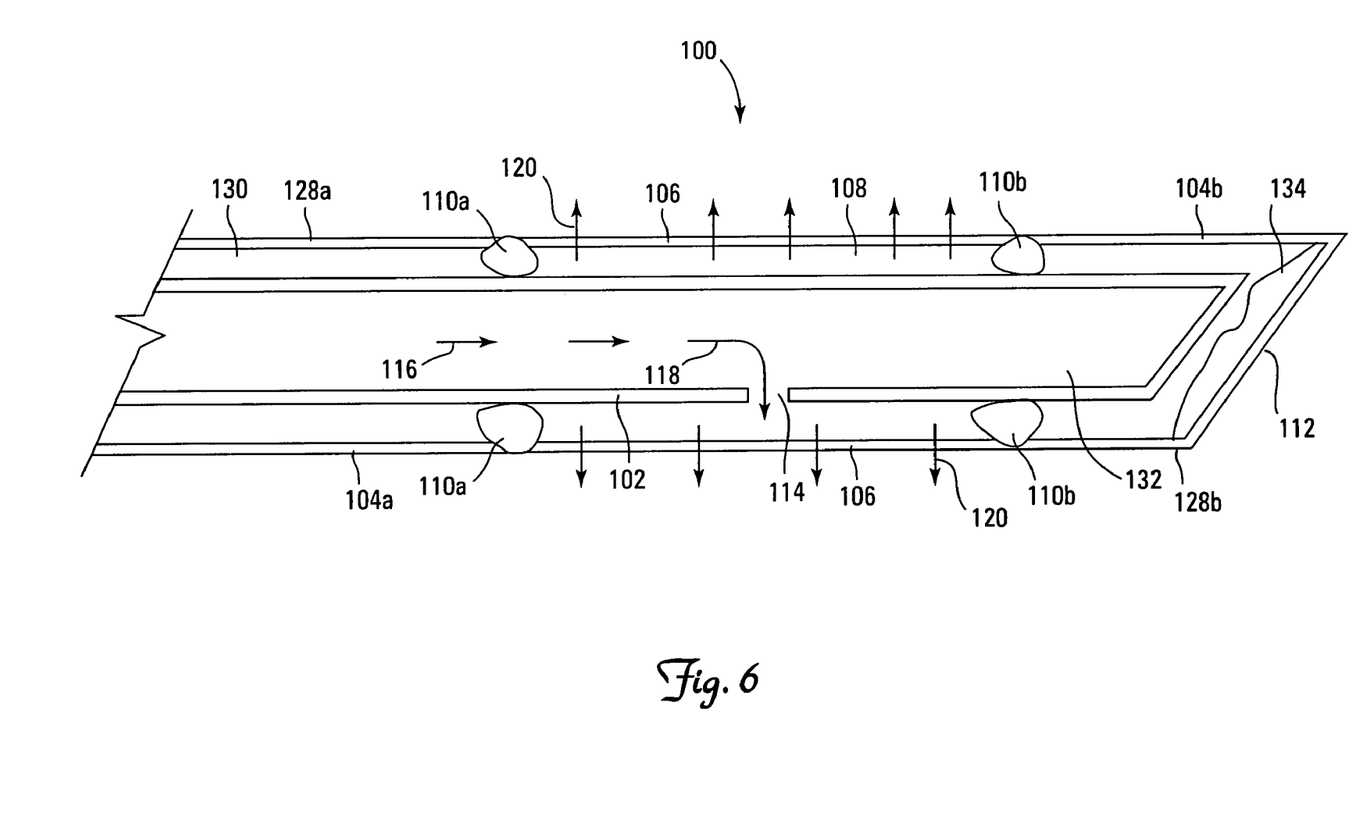
FIG. 6 is a cross sectional centerline view taken along the longitudinal axis of an embodiment of the injection/aspiration device, showing fluid passing through the semi-permeable membrane resulting from positive pressure applied to the lumen.
Figure 7:
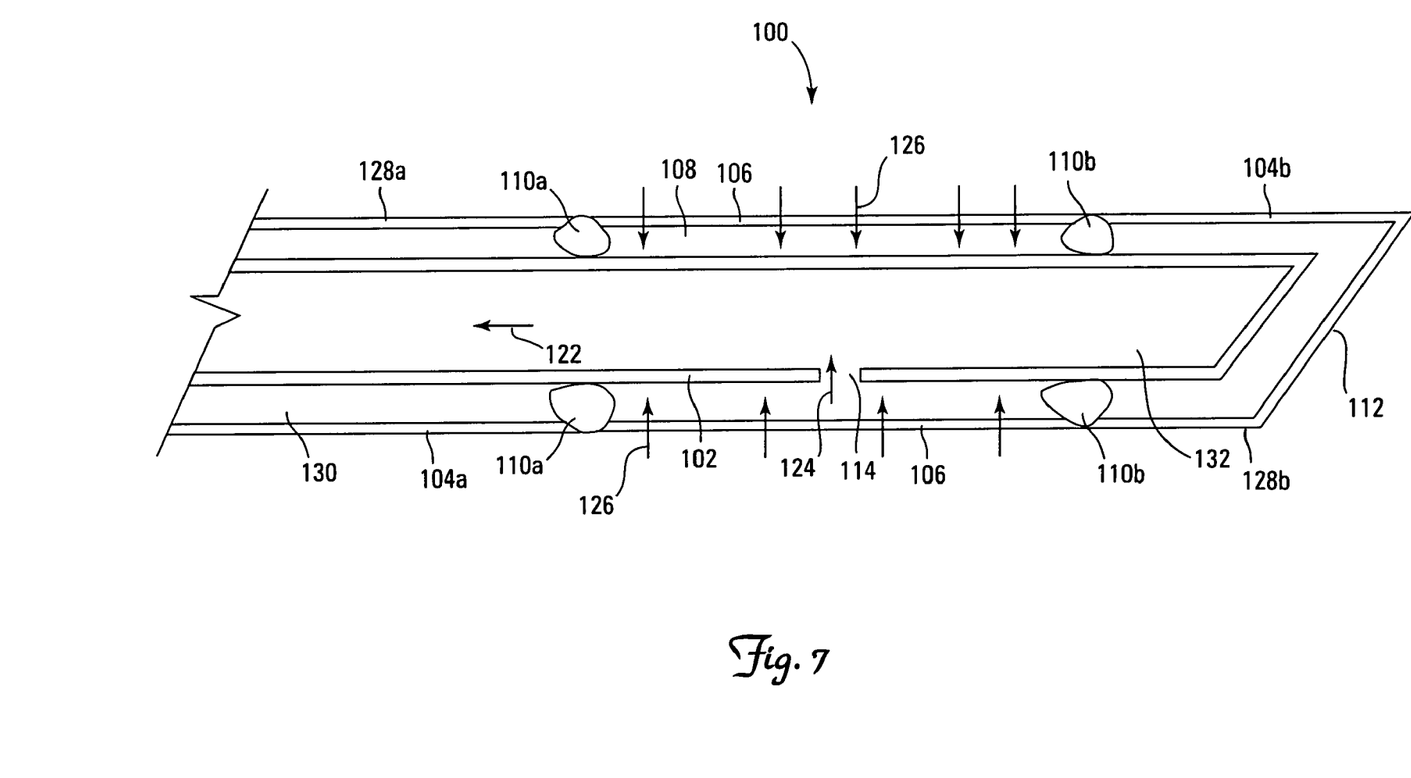
FIG. 7 is a cross sectional centerline view taken along the longitudinal axis of the injection/aspiration device shown in FIG. 6, showing fluid from a patient passing through the semi-permeable membrane into the fluid collection chamber, resulting from negative pressure applied to the lumen.

FIGS. 6 and 7 are cross sectional centerline views taken along the longitudinal axis (unnumbered) of an embodiment of the injection/aspiration device 100. A first hollow member 102 is formed from a substantially rigid material such as structural materials having a high modulus, including metals, polymers, (with and without fiber reinforcement) and ceramics and defines a first lumen 132 which allows fluid communication through the first hollow member 102. A second hollow member 104 (collectively) in one embodiment is formed in a proximal section 104a and a distal section 104b which are substantially concentrically aligned with the first hollow member 102 which is at least partially disposed inside the proximal and distal sections of the second hollow member 104a, 104b. In one embodiment, the proximal and distal sections of the second hollow member 104a, 104b each define an outer surface 128a, 128b and are linearly disposed to and do not contact each other. The proximal and distal sections of the second hollow member 104a, 104b function to further stiffen the injection/aspiration device 100 which allows it to more effectively be introduced into a patient without the use of other devices such as a needle, cannula, catheter, trocar or other introducers. In another embodiment (not shown) the second hollow member is not separated into individual pieces but maintains a structural connection throughout its length. A semi-permeable membrane 106 covers at least a single opening 114 and the space between the proximal 104a and distal 104b sections of the second hollow member to form a fluid collection chamber 108 between the first hollow member 102 and semi-permeable membrane 106. The semi-permeable membrane 106 is attached to the first hollow member 102 and proximal 104a and distal 104b sections of the second hollow member by a proximal layer 110a and a distal layer 110b of a bonding agent such as structural adhesives including but not limited to epoxies, urethanes, acrylics, polyimides and polysulfones. The opening 114 is formed through the first hollow member 102 allowing fluid communication between the first lumen 132 and fluid collection chamber 108 as depicted by arrow 118 (arrow 124 in FIG. 5). While the semi-permeable membrane 106 is shown in this embodiment as being co-planar with the exterior surfaces 128a, 128b of the proximal 104a and distal sections 104b of the second hollow member, the invention also contemplates having the semi-permeable membrane 106 placed on an interior surface (not shown) and is therefore within the scope of the invention. The distal end of the second hollow member 104b defines a distal end 112 which in this embodiment is sealed by plug 134.

The injection/aspiration device 100 shown in FIG. 6 is depicted by arrow 116 as having positive pressure applied to the first lumen 132. This results in fluid (not shown) moving distally through the first lumen 132 and ultimately through the opening 114 (as depicted by arrow 118), into the fluid collection chamber 108 and finally outward through the porous semi-permeable membrane 106 as depicted by arrow 120, at a uniform pressure and distribution to the intended treatment site of the patient following introduction.

The injection/aspiration device 100 shown in FIG. 7 is depicted by arrow 122 as having negative pressure applied to the first lumen 132. This results in fluid (not shown) moving through the semi-permeable membrane 106 as depicted by arrow 126, into the fluid collection chamber 108, through the opening 114 (as depicted by arrow 124), and finally into the lumen 132 where the fluid (not shown) is withdrawn.

Figure 8:
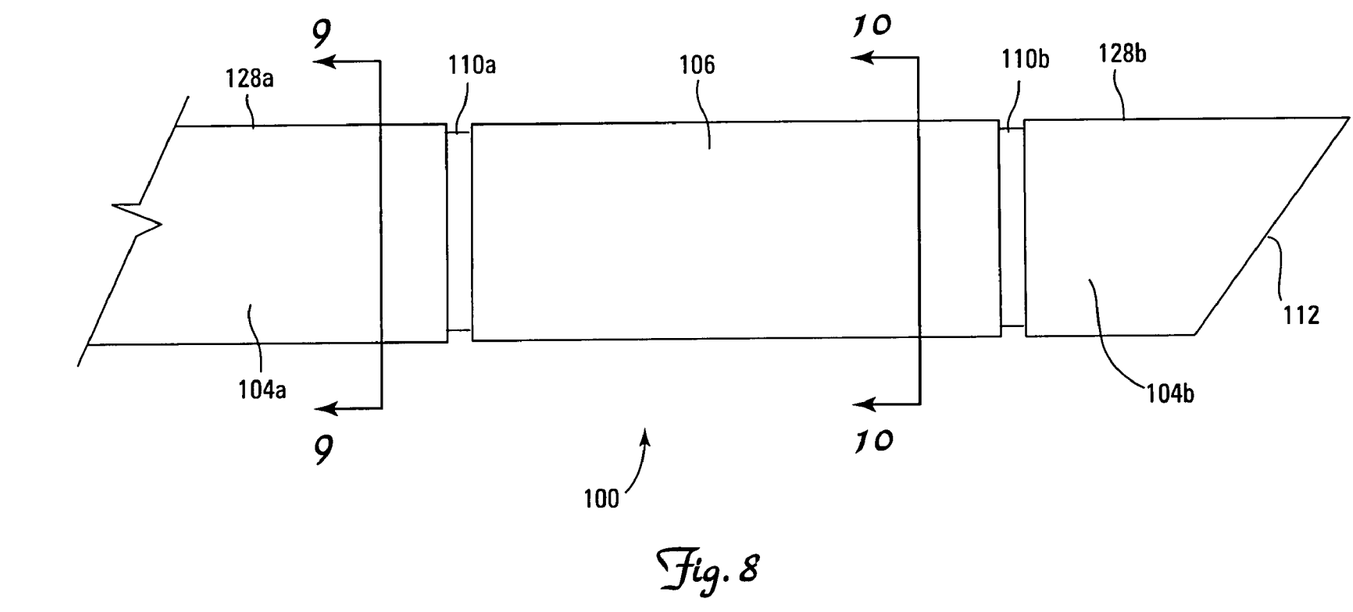
FIG. 8 is an external side view of the injection/aspiration device shown in FIGS. 6-7.

FIG. 8 is an external side view of the injection/aspiration device 100 prior to use. It is seen that in this embodiment the proximal 104a and distal 104b sections of the second hollow member 104 are linearly separated by the semi-permeable membrane 106 and do not contact each other. The semi-permeable membrane 106 and proximal 104a and distal 104b sections of the second hollow member 104 are attached to the first hollow member 102 (not shown in this figure) by means of a bonding agent 110a, 110b as discussed above. It is understood that the proximal end of the device (not shown) is provided with a connector 36 such as a Luer (not shown), barbed (not shown), or tapered tube (not shown) fitting allowing it to be connected with a fluid supply and pressure generating device such as a syringe 40. It is further understood that the device 100 could also be connected with a vacuum or aspirating device such as a mechanical pump (not shown) or hand operated syringe 40 when the device 100 is used for aspirating fluids.

Figure 9:
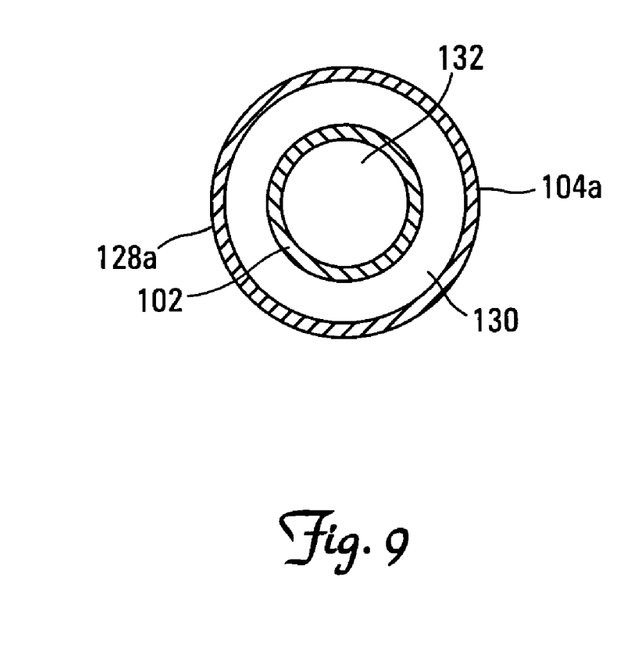
FIG. 9 is a cross sectional view of the injection/aspiration device shown in FIGS. 6-8 taken through line 9-9 of FIG. 8.

FIG. 9 is a cross section of the injection/aspiration device 100 taken through the line 9-9 as shown in FIG. 8. The first hollow member 102 is concentrically surrounded by the proximal section 104a of the second hollow member at the point where the cross section is taken. Concentricity of the first 102 and proximal section of the second 104a hollow members is proximally maintained by the Luer or other fitting (not shown) and distally by the bonding agent 110a which also serves to attach the semi-permeable membrane 106 (not shown this figure). It is understood that while a concentric, circular configuration is shown in the figures, this is for purposes of illustration only and many other shapes and/or configurations (not shown) could also be effectively used. Possible configurations include tubes, which are most common but could also include triangular, square, rectangular, other multi-segmented geometrical polygons, or composite profiles combining different lengths and/or shapes.

Figure 10:
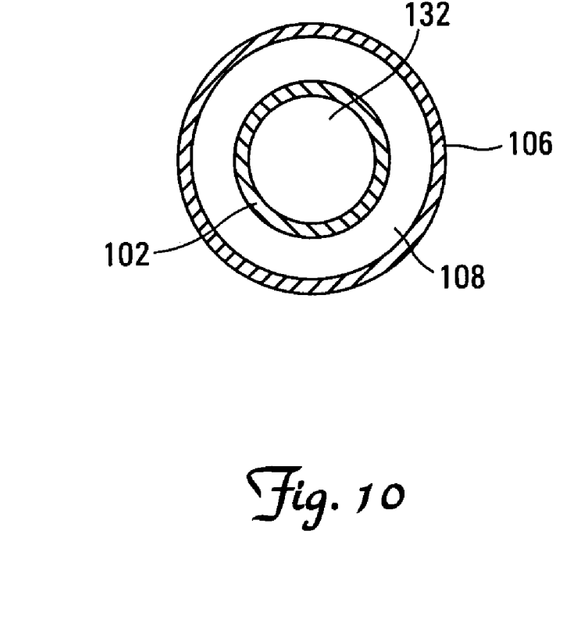
FIG. 10 is a cross sectional view of the injection/aspiration device shown in FIGS. 6-8 taken through line 10-10 of FIG. 8.

FIG. 10 is a cross section of the injection/aspiration device 100 taken through the line 10-10 as shown in FIG. 8. The first hollow member 102 is concentrically surrounded by the semi-permeable membrane 106 at the point where the cross section is taken. Concentricity of the first 102 hollow member and semi-permeable membrane 106 is proximally and distally maintained by the proximal and distal layers of the bonding agent 110a, 110b.

The first 102 and second 104 hollow members are typically formed from a material such as tubular stainless steel. First 102 and second 104 hollow members are initially cut to length followed by machining the ends for final uses that typically include a needle tip (unnumbered) used for penetrating tissue on the distal end 112 and a fitting 36 on the proximal end. The opening 114 is created by conventional machine cutting tools (e.g., drill bits) or other types of hole drilling processes such as laser machining. The first hollow member 102 is first attached to the fitting 36 by conventional methods well known to practitioners in the art, including but not limited to gluing, over-molding, or sonic welding. The proximal section of the second hollow member 104a is next slid over the first hollow member 102 and attached to the fitting 36 by conventional methods well known to practitioners in the art, including but not limited to gluing, over-molding, or sonic welding. A proximal layer of bonding agent 110a is applied between the proximal section of the second hollow member 104a and the first hollow member 102 which not only adheres the second hollow member 104a and the first hollow member 102 together but also allows a degree of control over the internal configuration (e.g., concentricity) of those elements. Next, the cut to length semi-permeable membrane 106 is slid over the first hollow member 102 and adhered to the first hollow member 102 at the point where the proximal layer of bonding agent 110a contacts both the semi-permeable membrane 106 and proximal section of the second hollow member 104a. Following this, a distal layer of bonding agent 110b is applied between the first hollow member 102 and the semi-permeable membrane 106 which similarly serves to not only adhere the semi-permeable membrane 106 to the first hollow member 102 but also allows a degree of control over the configuration thereof. The distal section of the second hollow member 104b is slid over the first hollow member 102 and affixed thereto by the distal layer of bonding agent 110b. If the sharpened distal end 112 of the second hollow member 104b has not been previously plugged with a filling material such as structural adhesive, solder or brazing alloys as described above, it should be done as a last step.

Figure 12:
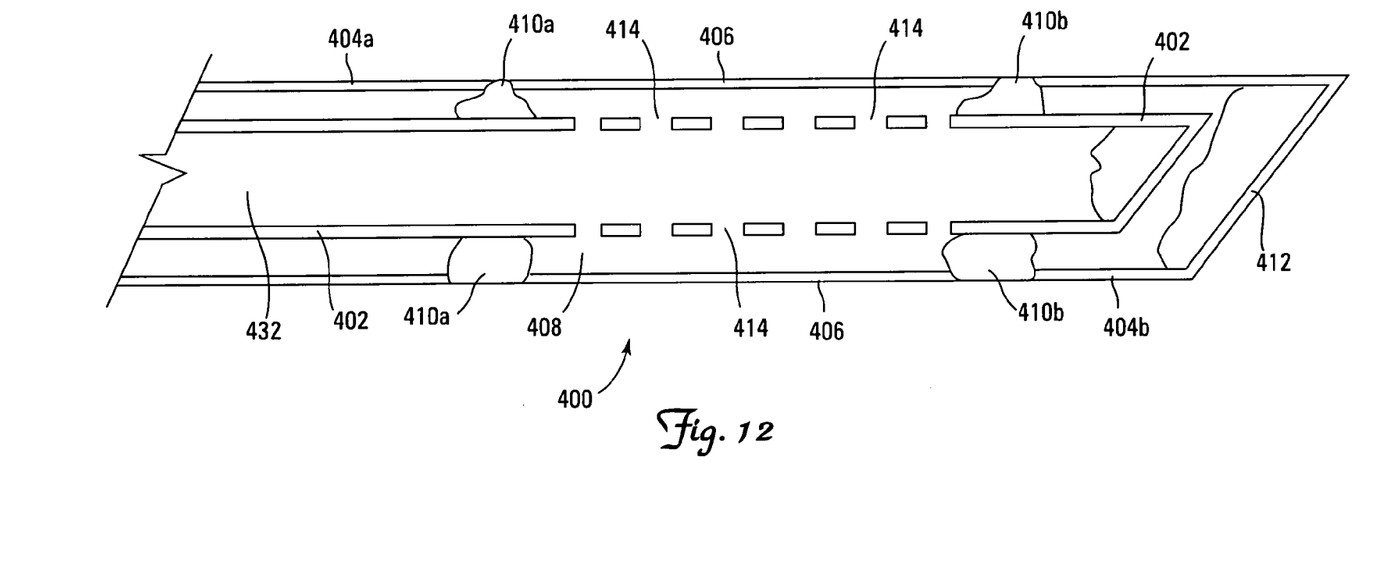
FIG. 12 is a cross sectional centerline view taken along the longitudinal axis of an embodiment of the injection/aspiration device having a plurality of openings in the first hollow member and is otherwise similar to the embodiment shown in FIGS. 6-10.

FIG. 12 is a cross sectional centerline view taken along the longitudinal axis of the hollow member of an embodiment of the injection/aspiration device 400 having a plurality of openings 414 in the hollow member 412. Other than having a plurality of openings 414 the injection/aspiration device 400 is similar to the injection/aspiration device 100 shown in FIGS. 6-10.

In one embodiment, the semi-permeable membrane 16, 106, 214, 406 can be made from a hollow fiber. Suitable materials for use as hollow fibers of the present invention provide an optimal combination of such properties as mass transfer properties, biocompatibility, surface-to-volume ratio, processability, hydrophobicity/hydrophilicity, strength, transport rate, and porosity. Examples of suitable hollow fibers are described in, for instance, I. Cabasso, "Hollow-Fiber Semi-permeable membranes", pp 598-599 in *Kirk Othmer Concise Encyclopedia of Chemical Technology*, which section is herein incorporated in its entirety.

The dimensions of a hollow fiber depend largely on the intended use of the apparatus. In a number of preferred embodiments, a hollow fiber is provided in the form of a capillary having an outer diameter of less than about one centimeter, and preferably less than about three millimeters, and whose outer, tissue contacting, wall functions as a semi permeable semi-permeable membrane. In most cases, a hollow fiber is used as a cylindrical semi-permeable membrane in a manner that permits selective exchange of materials across its walls.

In another embodiment, the semi-permeable membrane 16, 106, 214, 406 can be a modified microcatheter. Modified microcatheters can be prepared in any suitable manner, e.g., by microperforating an otherwise intact capillary or by spinning hollow fiber semi-permeable membranes from natural or synthetic polymers. Such fibers can be formed having any desired characteristics, e.g., isotropic (dense or porous) and anisotropic (asymmetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like. Other examples of suitable materials include membrane fibers such as those identified in the following table:

Use

Using the injection/aspiration device 10, 100, 200, 400 involves first preparing the patient for the procedure. Next, the device 10, 100, 200, 400 is removed from its sterile packaging and inserted through the patient's skin at a point convenient and proximate to the internal site of treatment. The inherently sharp and rigid nature of the device 10, 100, 200, 400 allows direct insertion through the patient's skin and other underlying tissue without the use of an additional introduction device such as a cannula, trocar, catheter, guide catheter, guide wire or other introducer. Obviating additional introducing devices necessitates shorter treatment times, decreased expense and a lesser probability of infection. In addition, introduction without introducing devices decreases the size of tissue access opening to the treatment site, thereby decreasing the morbidity, invasiveness and pain associated with the procedure.

When the desired treatment site is accessed for a procedure requiring positive fluid pressure, the device 10, 100, 200, 400 is connected to a fluid supply and/or pressure generating

| Types | Manufacturer | Catalog No. | Interior Diameter (um) | Wall Thickness (um) | Flow Rate (mL/min)/ Surface Area (sq. meter) | Porosity |
|---|---|---|---|---|---|---|
| Cuprophan | Baxter Haemodialysis Products | unknown | 200 | 8 | unknown | |
| Hemophan FoCus 160-H | Baxter Haemodialysis Products | unknown | 200 | 8 | unknown | |
| Spectra/Por Regenerated Cellulose Polyethylene Polypropylene Polysulfone | Spectrum 23022 La Cadena Drive, Suite #100 Laguna Hills, Ca. 92653 | #132-200 through 132-313 membrane types vary according to m.w., volume, pH, and chemical compatibility | 200 380 500 | 10-20 25 75 | 25-15 | 0.5 um 50 nm |
| Cellulose Triacetate CT-190 | Baxter Haemodialysis Products | CT-190 series #5M1546 CT-110-190 also available | 200 | unknown | unknown | |
| Cellulose Acetate CA-170 | Baxter Haemodialysis Products | CA-170 series #5M-1735 CA-150 - CA-170 series also available | unknown | unknown | unknown | |
| Polysulfone Hemoflow F-60A High Flux | Fresenius | F60 series #0500136A F3-6,8, 40-80 series also available | 200 | 40 | 40/1.3 | |
| Polysulfone Polyphen Capillary Membrane | Minntech | | 280 | 40 | | 0.45 um 0.10 um |
| Polyacrylo-nitrile (PAN) | Gambro-Health | | unknown | unknown | unknown | |
| Polyimide | UBE | unknown | unknown | unknown | unknown | unknown |
| Polysulfone | GE Healthcare | unknown | 0.5 mm (.45 um) 0.75 mm (.65 um) | unknown | unknown | 500,000 mwco |
| PVDF Polysulfone PAN | Koch | Unknown Unknown unknown | 0.5 mm & larger .043 inch | unknown | unknown | Up to 0.2 um Up to 500,000 mwco |
| PES   -phylic        -phobic PVDF | Membrana | Unknown Unknown unknown | 300 350 unknown | 100 85 unknown | unknown unknown | 0.5 um 0.5 um unknown |
| PVDF PP | Memcor/US filter | Unknown unknown | 500 unknown | 150 unknown | unknown | 0.04 to 0.1 um 0.1 um | device such as a syringe 40 which has been preloaded with a drug or therapeutic fluid required by the procedure. Placement of the device 10, 100, 200, 400 is determined to be correct by such methods as anatomical landmarks, ultrasound, CT guided introduction, MRI guided introduction, or an electrical signal. Positive pressure is applied to the lumen 20, 132, 220, 432 initially filling the empty lumen with the drug or therapeutic fluid. When the lumen 20, 132, 220, 432 is filled, the drug or therapeutic fluid is forced through the opening or openings 18, 114, 218, 414, into the fluid collection chamber 26, 108, 226, 408. The fluid collection chamber 26, 108, 226, 408 fills with the drug or therapeutic fluid which initially impedes flow and therefore buffers and equalizes the pressure and distribution of the weep rate of fluid from the device 10, 100, 200, 400. The drug or therapeutic fluid is eventually gently forced out through the porous semi-permeable membrane 14, 106, 214, 406 outside the device 10, 100, 200, 400 where it is taken up over a relatively large surface area of the surrounding tissues as required for treatment. Following completion of the procedure the device 10, 100, 200, 400 is removed from the patient, disconnected from the fluid supply and/or pressure generating device and disposed of.

When the desired treatment site is accessed for a procedure requiring negative fluid pressure, such as aspiration of excess fluid, the device 10, 100, 200, 400 is connected to a vacuum or aspirating device such as a mechanical pump or hand operated syringe 40. Placement of the device 10, 100, 200, 400 is determined to be correct by such methods as anatomical landmarks, ultrasound, CT guided introduction, MRI guided introduction, or an electrical signal. Negative pressure is applied to the lumen 20, 132, 220, 432 which extends to the fluid collection chamber 26, 108, 226, 408. A negative pressure potential is created which allows fluid surrounding the outer surface and region of the semi-permeable membrane 14, 106, 214, 406 to be drawn through the semi-permeable membrane 14, 106, 214, 406 through the opening or openings 18, 114, 218, 414 into the lumen 20, 132, 220, 432. Once in the lumen 20, 132, 220, 432 the fluid is proximally transported outside the device 20, 132, 220, 432 where it is disposed of or stored for further analysis. Following completion of the procedure the device 10, 100, 200, 400 is removed from the patient, disconnected from the fluid supply and/or pressure generating device and disposed of.

What is claimed is:

1. A catheter, comprising:
   a. a hollow member comprising a lumen, an outer surface, a distal end having a sharpened distal tip, and at least one opening through the hollow member allowing fluid communication between the lumen and the outer surface of the hollow member, the hollow member being sufficiently sharp and rigid to allow the catheter to be inserted through a patient's skin and underlying tissue without the use of another device; and
   b. a semi-permeable membrane attached to the hollow member and covering the at least one opening, the semi-permeable membrane defining a pore structure allowing fluid communication between the lumen and an area outside the semi-permeable membrane; and
   c. a fluid collection chamber between the outer surface of the hollow member and the semi-permeable membrane, wherein the catheter is adapted to move fluid through the fluid collection chamber under positive pressure and under neutral or less pressure.

2. The catheter of claim 1 wherein the pore size of the semi-permeable membrane is substantially uniform.

3. The catheter of claim 1 wherein the hollow member is tubular.

4. The catheter of claim 1 wherein the semi-permeable membrane is attached to the hollow member by a bonding agent.

5. The catheter of claim 3 wherein the semi-permeable membrane and the hollow member are concentrically disposed to each other.

6. The catheter of claim 1 wherein a plurality of openings extends between the lumen and the outer surface of the hollow member.

7. A catheter, comprising:
   a. a first hollow member comprising an outer surface, a lumen, a distal end, and at least one opening through the first hollow member allowing fluid communication between the lumen and the outer surface of the first hollow member;
   b. a proximal second hollow member section comprising a lumen sufficiently large to surround the the first hollow member, surrounding the first hollow member;
   c. a distal second hollow member section comprising a lumen sufficiently large to surround the first hollow member and a sharpened distal tip, surrounding the first hollow member and distal to the proximal second hollow member section: and
   d. a semi-permeable membrane attached to the first hollow member and covering the at least one opening, the semi-permeable membrane defining a pore structure allowing fluid communication between the lumen of the first hollow member and an area outside the semi-permeable membrane;
   wherein the first hollow member and proximal and distal second hollow member sections together are sufficiently rigid and wherein the distal tip of the distal second hollow member section is sufficiently sharp to allow the catheter to be inserted through a patient's skin and underlying tissue without the use of another device.

8. The catheter of claim 7 wherein the pore size of the semi-permeable membrane is substantially uniform.

9. The catheter of claim 7 wherein the first hollow member and the second hollow member are tubular.

10. The catheter of claim 7 wherein a fluid collection chamber is formed between the outer surface of the first hollow member and the semi-permeable membrane to allow the collection of fluid prior to exiting through the semi-permeable membrane when positive fluid pressure is applied to the lumen.

11. The catheter of claim 7 wherein when neutral or less pressure is applied to the lumen, fluid external to the catheter is drawn through the semi-permeable membrane, into a fluid collection chamber, through the opening and into the lumen.

12. The catheter of claim 7 wherein the semi-permeable membrane is attached to the hollow member by a bonding agent.

13. The catheter of claim 7 wherein a plurality of openings extends between the lumen and the outer surface of the first hollow member.

14. The catheter of claim 7 wherein the proximal second hollow member section is proximal to the first hollow member opening, and the distal second hollow member section is distal to the first hollow member opening.

15. The catheter of claim 14 wherein the proximal second hollow member section is proximal to the semi-permeable membrane and the distal second hollow member section is distal to the semi-permeable membrane.

16. The catheter of claim 12 wherein the semi-permeable membrane is attached to the outer surface of the first hollow member.

17. The catheter of claim 16 wherein the proximal and distal second hollow member sections are linearly disposed and separated by the semi-permeable membrane.

18. The catheter of claim 16 wherein the semi-permeable membrane surrounds the first hollow member.

* * * * *